United States Patent [19]
LaFortune et al.

[11] Patent Number: 5,669,901
[45] Date of Patent: Sep. 23, 1997

[54] ABSORBENT ARTICLE HAVING AN IMPROVED MECHANICAL FASTENING SYSTEM

[75] Inventors: Jeffrey Mark LaFortune, Appleton; Lynn Kirkpatrick LeMahieu, Hortonville, both of Wis.

[73] Assignee: Kimberly-Clark Worldwide, Inc., Neenah, Wis.

[21] Appl. No.: 634,542

[22] Filed: Apr. 18, 1996

[51] Int. Cl.$^6$ .................................................. A61F 13/15
[52] U.S. Cl. ........................ 604/391; 604/392; 24/306
[58] Field of Search ........................ 604/385.1, 391, 604/392, 393, 398; 24/306, 442–452

[56] References Cited

U.S. PATENT DOCUMENTS

| | | | |
|---|---|---|---|
| H1440 | 5/1995 | New et al. | 604/386 |
| 1,928,838 | 10/1933 | Marcus | 2/236 |
| 1,963,334 | 6/1934 | Neilson | 2/237 |
| 3,431,562 | 3/1969 | Souders | 2/221 |
| 3,500,478 | 3/1970 | Foster | 2/221 |
| 3,618,608 | 11/1971 | Brink | 128/287 |
| 3,688,348 | 9/1972 | Klotz et al. | 24/16 |
| 3,708,382 | 1/1973 | Erb | 161/48 |
| 3,745,588 | 7/1973 | Pehle et al. | 2/221 |
| 3,747,171 | 7/1973 | Montague, Jr. | 24/265 |
| 3,848,268 | 11/1974 | D'Ambrosio | 2/237 |
| 3,868,729 | 3/1975 | Lynam | 2/237 |
| 4,047,651 | 9/1977 | McMullen | 224/4 |
| 4,058,853 | 11/1977 | Boxer et al. | 2/239 |
| 4,114,297 | 9/1978 | Famolare, Jr. | 36/50 |
| 4,216,257 | 8/1980 | Schams et al. | 428/93 |
| 4,244,199 | 1/1981 | Rhode | 66/193 |
| 4,291,439 | 9/1981 | Riti | 24/119 |
| 4,294,238 | 10/1981 | Woodford | 128/80 |
| 4,315,508 | 2/1982 | Bolick | 604/392 |
| 4,388,075 | 6/1983 | Mesek et al. | 604/385 |
| 4,416,951 | 11/1983 | Mesnel | 428/586 |
| 4,488,316 | 12/1984 | Mosca | 2/171 |
| 4,500,316 | 2/1985 | Damico | 604/389 |
| 4,549,317 | 10/1985 | D'Ambrosio | 2/237 |
| 4,596,540 | 6/1986 | F'Geppert | 474/253 |
| 4,606,079 | 8/1986 | DeWoskin | 2/338 |
| 4,617,022 | 10/1986 | Pigneul et al. | 604/391 |
| 4,631,932 | 12/1986 | Sommers | 66/192 |
| 4,638,513 | 1/1987 | Woods | 2/268 |
| 4,643,729 | 2/1987 | Laplanche | 604/389 |
| 4,662,037 | 5/1987 | Provost et al. | 24/447 |
| 4,699,823 | 10/1987 | Kellenberger et al. | 428/219 |
| 4,728,553 | 3/1988 | Daniels et al. | 423/100 |
| 4,770,917 | 9/1988 | Tochacek et al. | 428/95 |
| 4,780,936 | 11/1988 | Brecher | 24/119 |
| 4,787,897 | 11/1988 | Torimae et al. | 604/389 |
| 4,831,997 | 5/1989 | Greene | 124/35 |
| 4,834,820 | 5/1989 | Kondo et al. | 156/73.3 |
| 4,861,322 | 8/1989 | Reddick | 474/254 |
| 4,862,563 | 9/1989 | Flynn | 24/442 |
| 4,870,725 | 10/1989 | Dubowik | 24/442 |

(List continued on next page.)

FOREIGN PATENT DOCUMENTS

| | | |
|---|---|---|
| 0364454B1 | 6/1993 | European Pat. Off. |
| 0640331A2 | 8/1993 | European Pat. Off. |
| 1597799 | 9/1981 | United Kingdom . |
| 2185383 | 7/1987 | United Kingdom . |
| 2206506 | 1/1989 | United Kingdom . |
| 2281100 | 2/1996 | United Kingdom . |
| 93/03644 | 3/1993 | WIPO . |
| 95/05140 | 2/1995 | WIPO . |
| 95/20930 | 8/1995 | WIPO . |

*Primary Examiner*—Mary Beth Jones
*Assistant Examiner*—Ki Yong O.
*Attorney, Agent, or Firm*—Patricia A. Charlier

[57] ABSTRACT

An absorbent article includes a fastening system that is easy for the wearer to remove but during use is adapted to resist pop-offs caused by clothing being applied or removed over the absorbent article. The fastening system includes an interlocking fastening component with a backing substrate having a grasping section, a primary attachment section, and secondary attachment sections transversely outward from the grasping section. A plurality of upstanding engaging elements such as hooks are disposed exclusively in the primary and secondary attachment sections.

14 Claims, 7 Drawing Sheets

U.S. PATENT DOCUMENTS

| | | | |
|---|---|---|---|
| 4,887,339 | 12/1989 | Bellanger | 24/575 |
| 4,894,060 | 1/1990 | Nestegard | 604/391 |
| 4,904,249 | 2/1990 | Miller et al. | 604/378 |
| 4,909,802 | 3/1990 | Ahr et al. | 604/385.1 |
| 4,931,343 | 6/1990 | Becker et al. | 428/95 |
| 4,938,754 | 7/1990 | Mesek | 604/385.2 |
| 4,941,237 | 7/1990 | Hovis | 24/304 |
| 4,964,860 | 10/1990 | Gipson et al. | 604/391 |
| 4,970,728 | 11/1990 | D'Ambrosio | 2/237 |
| 4,973,326 | 11/1990 | Wood et al. | 604/391 |
| 4,980,930 | 1/1991 | Cusimano | 2/220 |
| 4,999,853 | 3/1991 | Tanner | 2/321 |
| 5,010,595 | 4/1991 | Stradley | 2/227 |
| 5,019,065 | 5/1991 | Scripps | 604/391 |
| 5,019,073 | 5/1991 | Roessler et al. | 604/391 |
| 5,049,145 | 9/1991 | Flug | 604/391 |
| 5,053,028 | 10/1991 | Zoia et al. | 604/391 |
| 5,077,870 | 1/1992 | Melbye et al. | 24/452 |
| 5,147,343 | 9/1992 | Kellenberger | 604/368 |
| 5,176,671 | 1/1993 | Roessler et al. | 604/391 |
| 5,193,225 | 3/1993 | Karami et al. | 2/312 |
| 5,227,107 | 7/1993 | Dickenson et al. | 264/113 |
| 5,288,546 | 2/1994 | Roessler et al. | 428/284 |
| 5,304,162 | 4/1994 | Kuen | 604/391 |
| 5,325,569 | 7/1994 | Goulait et al. | 24/448 |
| 5,373,587 | 12/1994 | Sexton | 2/237 |
| 5,374,262 | 12/1994 | Keuhn, Jr. et al. | 604/391 |
| 5,386,595 | 2/1995 | Kuen et al. | 2/400 |
| 5,476,702 | 12/1995 | Datta et al. | 428/99 |

ABSORBENT ARTICLE HAVING AN IMPROVED MECHANICAL FASTENING SYSTEM

BACKGROUND OF THE INVENTION

The present invention relates to an absorbent article having an improved mechanical fastening system. More particularly, the invention pertains to an absorbent article that is maintained in place about a wearer by a fastening system that incorporates interlocking fastening components that are adapted to resist pop-offs and yet are easy to unfasten.

Absorbent articles such as adult incontinence products, training pants, diapers and sanitary napkins have been constructed with a wide variety of unique fastening systems. Among the most commonly employed fastening system are adhesive tape fasteners, garment attachment adhesives, straps with buttons, stretchable side panels, and interlocking fastening components. The type of fastening system is selected to maintain the particular product form in proper position until removed by the wearer or caregiver.

Over the last several years, fastening systems using interlocking fastening components have become more prevalent on commercial absorbent articles. The term interlocking fastening component refers to a material that refastenably connects to a mating material through the use of engaging elements so that the mating materials resist disengagement in a shear mode and allow disengagement in a peel mode. Hook-and-loop fasteners are the most widespread example of interlocking fastening components. The recent enthusiasm for fastening systems using interlocking fastening components is attributable in part to heightened consumer acceptance of interlocking fastening components, as well as improved performance and decreased cost of such materials.

Despite this increased popularity of absorbent articles that incorporate fastening systems with interlocking fastening components, these fasteners remain subject to failures during use. Fastener failures may include such undesired events as disassembly of the fastener components, non-refastenability, or the like. One particularly significant form of failure for fasteners with interlocking fastening components is a pop-off, which refers to the unintentional disengagement of the interlocking fastening components from one another during use of the absorbent article. Needless to say, this is particularly undesirable for the wearer given the nature of the product.

To date, there have been many attempts to reduce the frequency of pop-offs for fastening systems with interlocking fastening components. These efforts have focused on the engaging elements of the interlocking fastening components, and have resulted in an astounding variety in the size, shape and arrangement of the engaging elements. Despite these past attempts to improve performance, however, absorbent articles that incorporate fastening systems with interlocking fastening components continue to experience an unacceptably high level of pop-offs.

Furthermore, the feature of easily disengaging the mating materials must not be sacrificed in an attempt to reduce the level of pop-offs. Particularly for adult incontinence products, where the wearer may have a reduced degree of manual dexterity, ease of disengagement of interlocking fastening components is an important product attribute.

Therefore, what is lacking and needed in the art is an absorbent article that is maintained in place about the wearer by a fastening system with interlocking fastening components that are adapted to resist pop-offs and still are easy to unfasten.

SUMMARY OF THE INVENTION

In response to the discussed deficiencies in the prior art, a new absorbent article has been developed. The absorbent article utilizes a fastening system with interlocking fastening components and provides improved resistance to pop-offs without sacrificing the ease of removal.

In one aspect, the present invention concerns an absorbent article including a garment having first and second waist regions and an intermediate section which interconnects the waist regions. At least one first interlocking fastening component of the absorbent article is disposed in the first and second waist regions. The absorbent article also includes a pair of strap members that have opposite forward and rearward end portions. A second interlocking fastening component that is adapted to refastenably engage the first interlocking fastening component is attached to each of the forward and rearward end portions of each strap member. Each second interlocking fastening component has a longitudinal axis, a proximal edge, a distal edge longitudinally spaced from the proximal edge and first and second side edges extending between the proximal and distal edges. Each second interlocking fastening component includes a backing substrate having a grasping section contiguous with the distal edge, a primary attachment section longitudinally disposed between the grasping section and the proximal edge, and secondary attachment sections disposed between the grasping section and each of the first and second side edges. Each second interlocking fastening component also includes a plurality of upstanding engaging elements disposed exclusively in the primary attachment section and each of the secondary attachment sections.

In another aspect, the present invention concerns an absorbent article including a garment having first and second waist regions and an intermediate section which interconnects the waist regions. At least one first interlocking fastening component is disposed in the first waist region. At least one second interlocking fastening component is bonded to the second waist region and adapted to refastenably engage the first interlocking fastening component. The second interlocking fastening component has a longitudinal axis, a proximal edge, a distal edge longitudinally spaced from the proximal edge, and first and second side edges extending between the proximal and distal edges. The second interlocking fastening component includes a backing substrate having a grasping section contiguous with the distal edge, a primary attachment section longitudinally disposed between the grasping section and proximal edge, and secondary attachment sections disposed between the grasping section and each of the first and second side edges. A plurality of upstanding engaging elements are disposed exclusively in the primary attachment section and each of the secondary attachment sections.

The absorbent articles may be in the form of adult incontinence products, training pants, diapers, sanitary napkins, or the like. Typically, the absorbent articles include a moisture barrier, an absorbent assembly disposed on the moisture barrier, and a bodyside liner bonded to the moisture barrier and sandwiching the absorbent assembly therebetween. Such absorbent articles are generally positioned in the crotch area and worn beneath underpants or other clothing.

While the absorbent article is worn, the wearer or caregiver may apply or remove underpants or other clothing over the product. For example, clothing may be pulled over the absorbent article when initially putting on the product, changing clothes, going to the bathroom, checking or adjusting the product, or removing the product. Applicant has discovered that failure of the garment fastening system due to a pop-off of an interlocking fastening component is significantly more likely to result when the wearer is changing or adjusting clothing for these purposes than when the wearer is involved in activities such as walking, running, sleeping or sitting. Applicant theorizes that the movement of clothing over the resilient interlocking fastening components greatly increases the likelihood of pop-offs. In particular, elastic waistbands included in underpants, pantyhose, or other clothing tend to catch on the edges and corners of resilient interlocking fastening components and cause pop-offs.

Applicant has discovered that absorbent articles including interlocking fastening components as described above and set forth in greater detail below minimize the occurrences of pop-offs when clothing is raised or lowered over the absorbent article. The upstanding engaging elements disposed in the secondary attachment sections function to securely attach the corners of the second interlocking fastening components to the first interlocking fastening components. The corners of the second interlocking fastening components are thereby less likely to become disengaged by clothing or other materials passing over the garment fastening system. At the same time, the second interlocking fastening components can be easily disengaged from the first interlocking fastening components due to the presence and location of the grasping sections. The grasping sections allow the wearer to easily insert a finger or fingernail between the first and second interlocking fastening components and initiate the peeling motion needed to disengage the mating materials.

In particular embodiments of the present invention, the grasping section has a surface area of at least about 10 percent, such as from about 10 to about 25 percent, of the toll useable surface area. Further, the grasping section desirably incorporates a maximum width dimension of at least about 1.5 centimeters and a maximum length dimension of at least about 0.6 centimeters. Further, each of the secondary attachment sections desirably has a surface area of at least about 2 percent, such as from about 5 to about 10 percent, of the total useable surface area.

In another aspect, the invention pertains to an absorbent article including a garment and a pair of strap members. Each strap member includes second interlocking fastening components adapted to refastenably engage first interlocking fastening components on the garment. Each second interlocking fastening component has a backing substrate with a grasping section disposed between proximal and distal edges, a first lateral region contiguous with a first side edge, and a second lateral region contiguous with a second side edge. A plurality of upstanding engaging elements are disposed exclusively in the first and second lateral regions.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DETAILED DESCRIPTION OF THE PREFERRED EMBODIMENT

Figure 6:
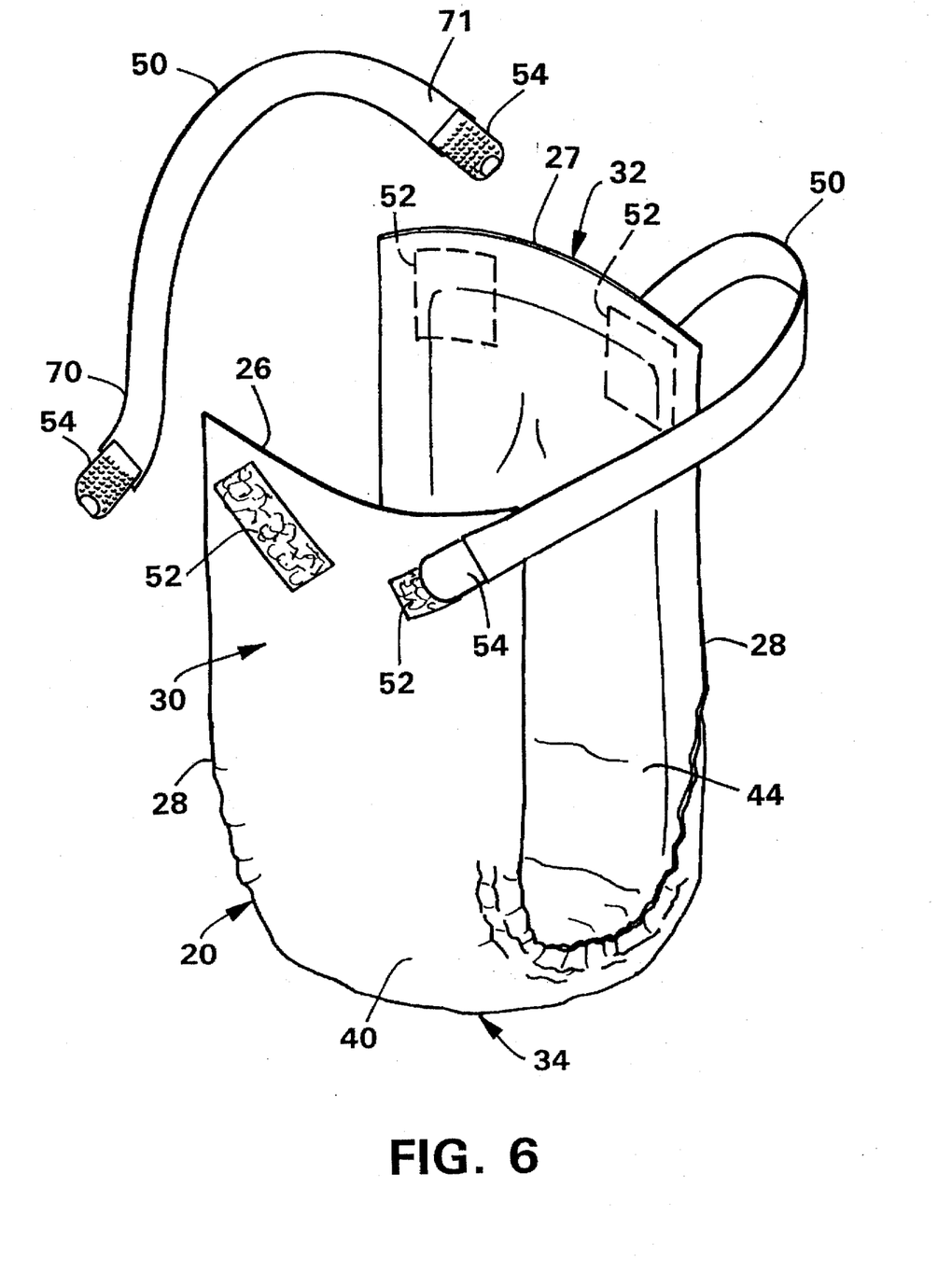
FIG. 6 representatively shows a perspective view of a disposable absorbent article according to the present invention, including two of the strap members illustrated in FIG. 1.

With reference to FIGS. 1, 2, 6 and 7, an absorbent article formed according to the invention is shown for purposes of illustration as a disposable undergarment 20 for adult incontinence which is maintained in position about a wearer by an attachment system comprising a pair of strap members 50. As used herein, the term "disposable" includes being disposed of after use and not intended to be washed and reused. The undergarment 20 is shown in FIG. 6 to illustrate the position the undergarment assumes during use. The invention may also be embodied in other types of garments, such as other disposable absorbent articles, reusable absorbent articles, or the like.

Figure 2:
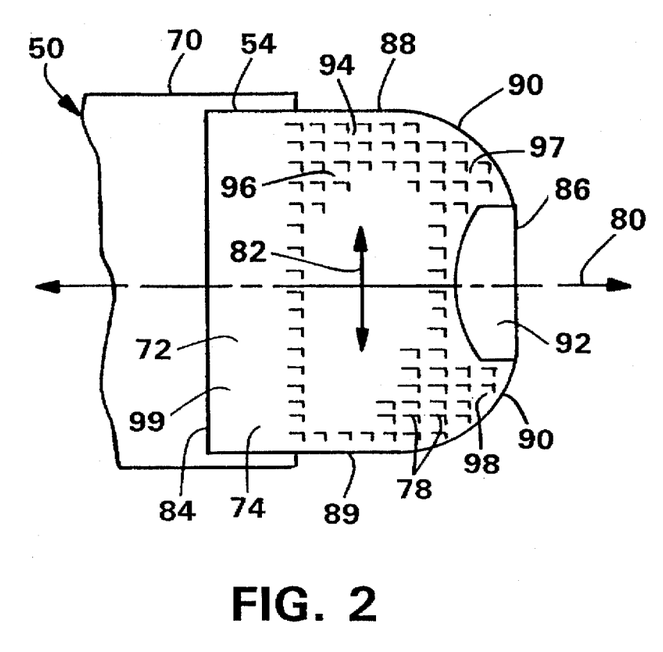
FIG. 2 representatively shows an enlarged plan view of one end portion of the strap member shown in FIG. 1.

In general, the undergarment 20 includes first interlocking fastening components 52 disposed on the undergarment 20 and second interlocking fastening components 54 bonded to the strap members 50. The second interlocking fastening components 54 have opposite proximal and distal edges 84 and 86 and side edges 88 and 89 that extend between the proximal and distal edges (FIG. 2). The second interlocking fastening components 54 comprise a backing structure 72 and a plurality of engaging elements 78 that project from the backing structure. The engaging elements 78 are disposed exclusively in a primary attachment section 96 and secondary attachment sections 97 and 98. A grasping section 92 of the second interlocking fastening component 54 is provided to facilitate removal of the second interlocking fastening component from the first interlocking fastening component 52.

Figure 7:
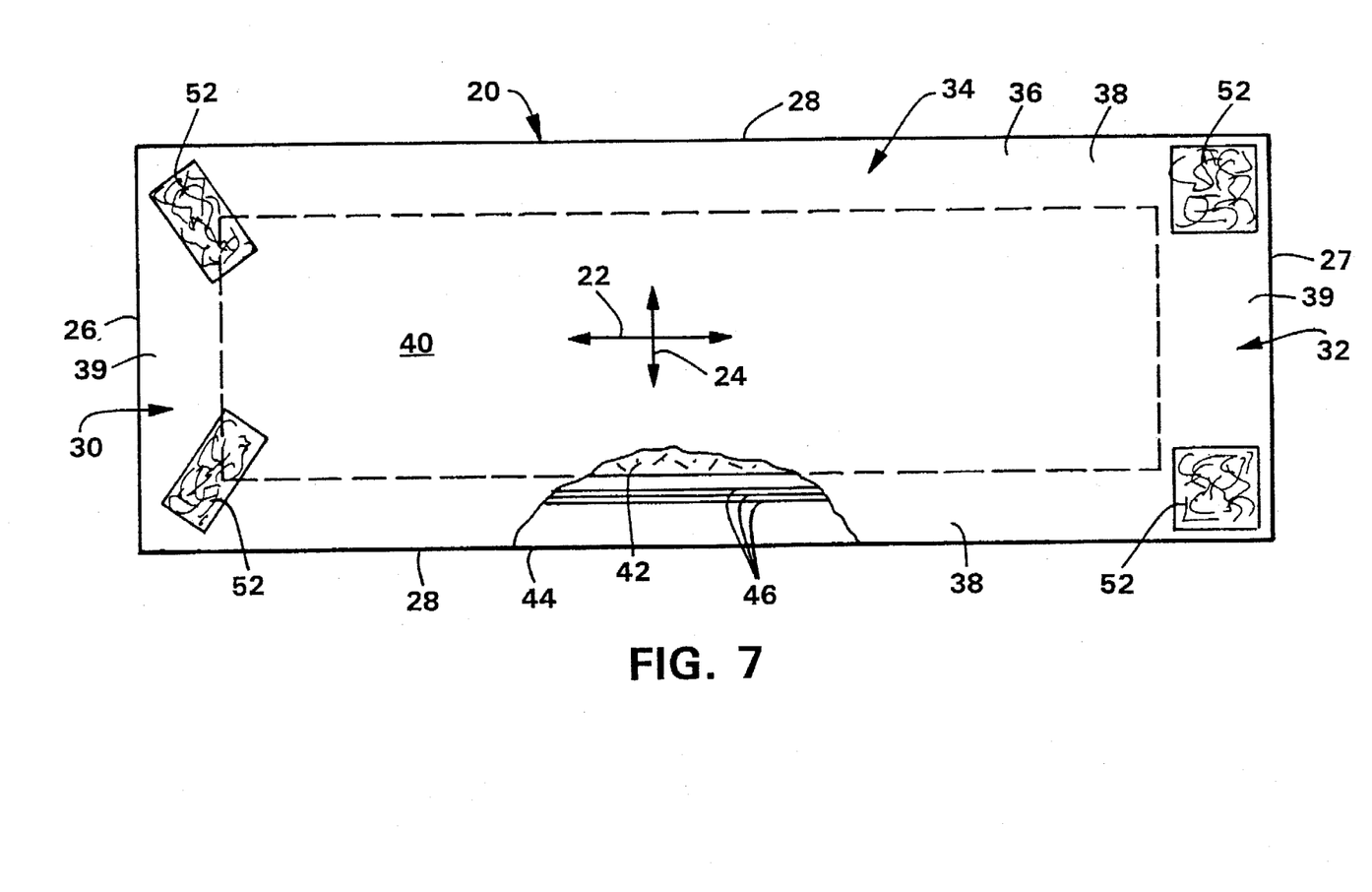
FIG. 7 representatively shows a plan view of a garment portion of the absorbent article shown in FIG. 6, taken from the outer garment side of the absorbent article in a stretched and laid flat condition and with portions broken away for purposes of illustration.

With reference particularly to FIG. 7, the illustrated undergarment 20 defines a longitudinal axis or center line represented by arrow 22 and a transverse axis or center line represented by arrow 24. The longitudinal axis 22 generally corresponds to the machine direction of the garment during manufacture and the greatest planar dimension of the product. The undergarment 20 has opposite, front and back longitudinal end edges 26 and 27, and longitudinal side edges 28 that extend between the longitudinal end edges.

The undergarment 20 includes a first or front waist region 30, a second or back waist region 32, and an intermediate, crotch region 34 positioned between and interconnecting the front and back waist regions.

The outer edges of the undergarment 20 define a periphery 36 in which the longitudinally extending side margins are designated 38 and the laterally extending end margins are designated 39. The end edges 26 and 27 and side edges 28 are shown as generally straight, but optionally, may be curvilinear and contoured.

The front waist region 30 is contiguous with the front end edge 26 and extends longitudinally inward therefrom toward the transverse center line 24 of the undergarment 20. The back waist region 32 is contiguous with the back end edge 27 and extends longitudinally inward therefrom toward the transverse center line 24. The waist regions 30 and 32 comprise those upper portions of undergarment 20 which, when worn, wholly or partially cover or encircle the waist or mid-lower torso of the wearer. The intermediate, crotch region 34 comprises that portion of undergarment 20 which, when worn, is positioned between the legs of the wearer and covers the lower torso of the wearer. Thus, the crotch region 34 is the area where insults of urine typically occur in the undergarment or other disposable absorbent article.

The undergarment 20 includes a substantially liquid impermeable moisture barrier 40, an absorbent assembly 42 disposed on the moisture barrier, and a substantially liquid permeable bodyside liner 44 bonded to the moisture barrier to sandwich the absorbent assembly therebetween (FIG. 7). The moisture barrier 40 and bodyside liner 44 are desirably longer and wider than the absorbent assembly 42 so that the peripheries of the moisture barrier and bodyside liner may be bonded together using ultrasonic bonds, thermal bonds, adhesives, or other suitable means. The peripheries of the moisture barrier 40 and the bodyside liner 44 typically form the side and end margins 38 and 39 of the undergarment 20. The absorbent assembly 42 may be bonded directly to the moisture barrier 40 and/or the bodyside liner 44 using ultrasonic bonds, thermal bonds, adhesives, or other suitable means. As used herein, the term "bonded" refers to the joining, adhering, connecting, attaching, or the like, of two elements. Two elements will be considered to be bonded together when they are bonded directly to one another or indirectly to one another, such as when each is directly bonded to intermediate elements. The terms "disposed," "disposed on," "disposed with," "disposed at," "disposed near" and variations thereof are intended to mean that one element can be integral with another element, or that one element can be a separate structure bonded to or placed with or placed near another element.

The moisture barrier 40 desirably comprises a material that is formed or treated to be liquid impermeable. Alternatively, the moisture barrier 40 may comprise a liquid permeable material and other suitable means may be provided to impede liquid movement away from the absorbent assembly, such as a liquid impermeable layer (not shown) associated with the absorbent assembly 42. The moisture barrier 40 may also be gas permeable, such that gases encountered during use of the absorbent garment are able to pass through the material under ordinary use conditions, over either all or part of its surface area.

The moisture barrier 40 may comprise a single layer of material or a laminate of two or more separate layers of material. Suitable moisture barrier materials include films, wovens, nonwovens, laminates of films, wovens, and/or nonwovens, or the like. For example, the moisture barrier 40 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 40 is a polyethylene film that has a nominal thickness of about 0.025 millimeter and a systematic matte embossed pattern, and that has been corona treated on both sides. Another suitable moisture barrier material is an adhesive or thermal laminate comprising a cast or blown film formed of polypropylene, polyethylene or the like, and a spunbond web formed of polypropylene and polyethylene bicomponent fibers in a 50/50 side-by-side configuration.

The absorbent assembly 42 comprises materials adapted to absorb and retain liquid waste. The absorbent assembly 42 may comprise various absorbent materials, such as an airformed batt of cellulosic fibers (i.e., wood pulp fluff) or a coform material composed of a mixture of cellulosic fibers and synthetic polymer fibers. Polymer fibers may be incorporated, for example, in the manner described in U.S. Pat. No. 5,227,107 issued Jul. 13, 1993, to Dickenson et al. The absorbent assembly 42 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. Nos. 4,699,823 issued Oct. 13, 1987, to Kellenberger et al. and U.S. Pat. No. 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 42 may also include tissue layers or acquisition or distribution layers to help maintain the integrity of fibrous absorbents or transport liquids (not shown).

The bodyside liner 44 is formed of a liquid permeable material so that liquid waste, and possibly semi-solid waste as well, can pass through the liner and be absorbed by the absorbent assembly 42. Suitable bodyside liners 44 may comprise a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 44 is desirably nonelastic and may be treated with a surfactant to aid in liquid transfer. In a particular embodiment of the invention, the liner 44 comprises a nonwoven, spunbond polypropylene fabric composed of about 2.8–3.2 denier fibers formed into a web having a basis weight of about 22 gsm and density of about 0.06 gm/cc. The fabric is surface treated with about 0.28 weight percent of a surfactant commercially available from Rohm and Haas Co. under the trade designation Triton X-102. As used herein, the term "fabric" is used to refer to all of the woven, knitted and nonwoven fibrous webs. The term "nonwoven web" means a web of material which is formed without the aid of a textile weaving or knifing process.

The undergarment 20, which is in a stretched and laid flat condition in FIG. 7, is illustrated as having a rectangular periphery 36. Of course, the undergarment 20 may optionally be hourglass-shaped, I-shaped, T-shaped, or irregularly-shaped. The general shape of the absorbent assembly 42 may correspond to the shape of the undergarment 20 or assume a different shape. For example, the undergarment 20 may include a relatively short absorbent assembly and separate liquid handling layers in the waist regions (not shown) as disclosed in U.S. patent application Ser. No. 08/515,505 titled "Absorbent Article Having Improved Waist Region Dryness And Method Of Manufacture" and filed Aug. 15, 1995 by L. LeMahieu et al. (Attorney Docket No. 12,248) and assigned to the assignee of the present application.

Desirably although not necessarily, the undergarment 20 also includes leg elastic members 46 (FIG. 7) to draw and hold the side margins 38 of the undergarment 20 against the legs of the wearer and form a seal therewith. As used herein, the terms "elastic," "elasticized" and "elasticity" mean that property of a material by virtue of which it tends to recover its original size and shape after removal of a force causing a deformation. The elongated leg elastic members 46 are longitudinally orientated in each side margin 38, extending toward the front and back end edges 26 and 27. The leg elastic members 46 are positioned in the illustrated embodiment between the moisture barrier 40 and the bodyside liner 44. Using ultrasonic bonds, adhesives, thermal bonds, or other suitable means, the leg elastic members 46 are attached in a stretched condition to the moisture barrier 40, the bodyside liner 44, or both, in either a straight or a curved shape. Alternatively, the leg elastic members 46 may be attached in a relaxed state to a gathered portion of the moisture barrier 40, the bodyside liner 44, or both.

The leg elastic members 46 may be formed of a dry-spun coalesced multifilament elastomeric thread sold under the tradename LYCRA® and available from E.I. Du Pont de Nemours and Company. Alternately, the elastic members may be formed of other typical elastics utilized in the undergarment-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 40 and the liner 44. Other suitable elastic gathering means are disclosed in U.S. Pat. Nos. 4,938,754 to Mesek and U.S. Pat. No. 4,388,075 to Mesek et al.

The attachment system in the illustrated embodiment includes a pair of strap members 50 that are releasably attached to the front and back waist regions 30 and 32 to support the undergarment 20 about the body of the wearer. Attachment systems of this general type are disclosed in U.S. Pat. No. B1 4,315,508 to Bolick, which is incorporated herein by reference. The present fastening system, which is designed to releasably attach the strap members 50 to the undergarment 20 with a minimum number of pop-offs during use and be easy for the wearer to release, will now be described in greater detail.

The illustrated fastening system includes a plurality of first and second interlocking fastening components 52 and 54 that are adapted to refastenably connect to one another. The first interlocking fastening components 52 consist of four separate elements bonded to the moisture barrier 40, and the second interlocking fastening components 54 consist of four separate elements bonded to the two strap members 50.

The interlocking fastening components 52 and 54 have surfaces that are refastenably connectable. The term "refastenably connectable" and variations thereof are used herein to mean that the surfaces are adapted to repeatedly, releasably engage one another. Specifically, one surface of each of the interlocking fastening components 52 and 54 comprises a plurality of engaging elements that project from that surface. The engaging elements of one interlocking fastening component 52 or 54 are adapted to repeatedly engage and disengage the engaging elements of the other interlocking fastening component. Suitable engaging elements for such interlocking materials include self-engaging geometric shaped materials, such as hooks, loops, bulbs, mushrooms, arrowheads, balls on stems, male and female mating components, or the like. As used herein, the term "releasably engaged" and variations thereof refer to two elements being connected or connectable such that the elements tend to remain connected absent a separation force applied to one or both of the elements, and the elements being capable of separation without substantial permanent deformation or rupture.

The engagement of the components 52 and 54 is accomplished mechanically rather than adhesively, and the components are adapted to resist disengagement in a shear mode yet release relatively easily from one another in a peel mode. The shear mode of a fastener release refers to forces tending to separate the mechanical interlocking fastening components (such as a hook-and-loop material) when the components are subjected to opposing forces in the plane of attachment of the components, and the peel mode of a fastener release refers to forces tending to separate the mechanical interlocking fastening components when one component is subjected to a force perpendicular to the plane of attachment of the components. As used herein, the term "force" includes a physical influence exerted by one body on another which produces acceleration of bodies that are free to move and deformation of bodies that are not free to move.

In the illustrated embodiment, the first interlocking fastening components 52 are formed of a loop material and will also be referred to as loop fasteners 52, and the second interlocking fastening component 54 are formed of a hook material and will also be referred to as hook fasteners 54. These fasteners 52 and 54 comprise the complementary, mating components of a hook-and-loop fastening system.

Figure 8:
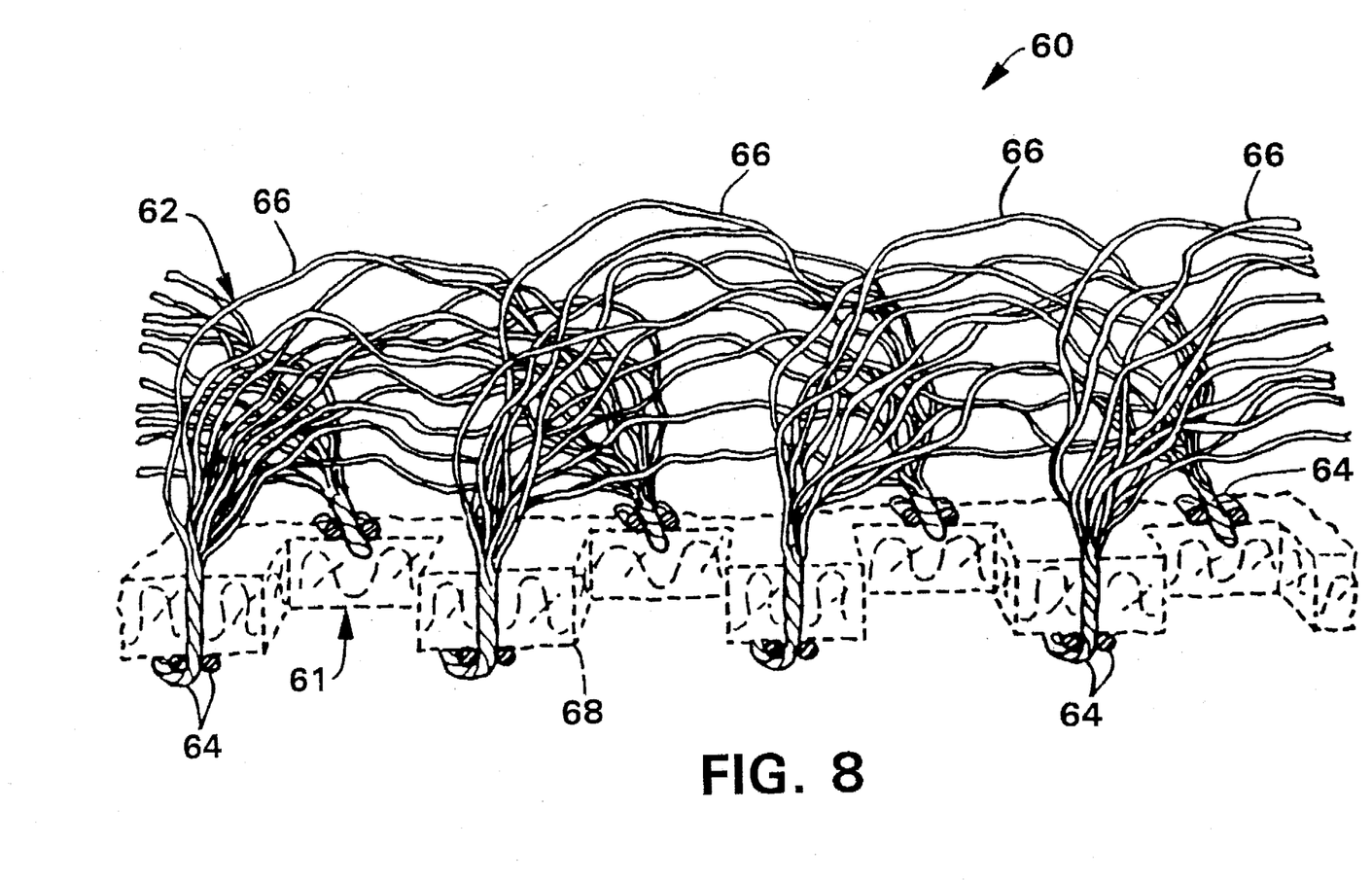
FIG. 8 representatively shows an enlarged section view of an exemplary loop material.

The term "loop material" is intended to mean any fabric having a base or backing structure and a plurality of loop members extending upwardly from at least one surface of the backing structure. An illustrative loop material 60 is representatively shown in FIG. 8. The loop material 60 is a flexible fabric material having opposite major surfaces designated first major surface 61 and second major surface 62. The loop material 60 comprises yarns 64 that are arranged to provide a raised loop construction in which the fabric is stabilized so that engaging elements, that is loops 66, are erect from the fabric backing 68. As used herein, the term "flexible" refers to materials which are compliant and which will readily conform to the general shape and contours of the wearer's body.

The loop material 60 may be formed of any suitable material, such as acrylic, nylon or polyester, and may be formed by methods such as warp knifing, stitch bonding or needle punching. The loop material 60 can be stabilized through napping, thermosetting or the like so that the individual loops 66 are erect from the fabric base 68. The loop fasteners 52 can also be any suitable material having non-woven loops thereon. The loop material 60 may optionally include a sizing (not shown), such as a vinyl acetate copolymer sizing available from National Starch and Chemical Corp. under the trade designation RESYN 5904, applied by mist deposition or other suitable means to the backing 68 to a final concentration of less than about 4 weight percent.

In a preferred embodiment, the first interlocking fastening components 52 are formed of a loop material 60 having a two bar warp knit construction, with from 21 to 41 courses per inch (8–16 per cm.) and from 26 to 46 wales per inch (10–18 per cm.), of polyester yarn. In particular, about 15–35 percent of the yarns may be composed of yarn having about 1–30 individual filaments therein and having a yarn denier within the range of about 15–30 d (denier). In addition, about 65–85 percent of the yarns may be composed of yarn having about 1–30 individual filaments therein and having a yarn denier within the range of about 20–55 d. Also, the loops may particularly be formed with a loop height from about 2 to about 2.5 millimeters. The loop caliper may be from about 0.010 to about 0.040 inch (0.25–1 ram.) and the basis weight may be from about 1.0 to about 3.0 ounces per square yard (34–102 grams per square meter). One particular loop material 60 which has been found suitable for the loop fasteners 52 is identified as No. 19902 and is available from Guilford Mills of Greensboro, N. C.

As shown in FIGS. 6 and 7, the first interlocking fastening components or loop fasteners 52 are bonded to the surface of the moisture barrier 40 that is remote from the bodyside liner 44. Each of the loop fasteners 52 is rectangular, although the loop fasteners may alternatively be square, round, oval, curved or otherwise nonrectangulary shaped. The loop fasteners 52 in each waist region 30 and 32 are desirably separated from one another and positioned adjacent the opposite sides edges 28. Desirably although not necessarily, the loop fasteners 52 are also spaced from the front and back end edges 26 and 27 and the side edges 28 by at least about 0.25 inch (6.5 mm.). Alternatively, them may be a greater number or a lesser number of loop fasteners 52 bonded to the moisture barrier 40 (not shown) as long as there is at least one interlocking fastening component disposed in the first and second waist regions. Still alternatively, the moisture barrier itself may be constructed of an interlocking material so that the strap members 50 may be attached directly to the moisture barrier (not shown).

The loop fasteners 52 in the front and back waist regions 30 and 32 may be the same size and be symmetrically positioned. More desirably, however, it has been determined that the particular loop fasteners 52 disclosed herein provide adjustability for the attachment system and at the same time promote the proper orientation of the undergarment 20 on the wearer. In particular, the loop fasteners 52 are desirably attached at specified angles in relation to the longitudinal and transverse axes 22 and 24 of the undergarment 20 in order to promote a proper orientation of the garment on the wearer.

The loop fasteners 52 in the front waist region 30 are desirably rectangular in shape measuring approximately 1.25 inches by 3.38 inches (3 by 9 cm.). Each loop fastener 52 in the front waist region 30 is bonded to the moisture barrier 40 such that the longitudinal axis of the fastener is directed generally toward the nearest corner of the undergarment 20 and forms an angle in the range of from about 25 to about 45 degrees with the transverse axis 24. The term "longitudinal axis" in reference to the fastener 52 is used to man the axis parallel to the longer dimension of the fastener.

Each loop fastener 52 in the back waist region 32 is desirably at least 1 inch by 1 inch (25 by 25 mm.), providing a surface area of at least about 1 in² (6.45 cm²). For example, the loop fasteners 52 in the back waist region 32 may be rectangular and measure 1.5 inch by 2.0 inch (38 by 51 ram.), with the longer dimension of the fastener aligned with the transverse axis 24 of the undergarment 20. Alternately, the loop fasteners 52 in the back waist region 32 could be formed as a single pad of loop material attached across the back waist region 32 (not shown).

The loop tip orientation of the loop fasteners 52 has been found to affect performance of the attachment system. The preferred loop material 60 will have a loop tip orientation (not shown) in a single direction. As used herein, "loop tip orientation" refers to the general direction in which the tips of the loop members 66 are bent. This direction, which will be in the plane of the loop material, is caused by the napping process used to make the loop material. However, the loop tip orientation may be generated by other processes as well, such as brushing, scraping, nipping, rolling, pressing, differential crepeing, combing and so forth. The loop tip orientation of a loop material can be established by selecting appropriate manufacturing processes and equipment as known in the art.

Desirably, the loop tip orientation of either loop fastener 52 in the front waist region 30 is generally perpendicular to the longitudinal axis of the fastener and directed toward the front end edge 26 of the undergarment 20. Furthermore, the loop tip orientation of either loop fastener 52 in the back waist region 32 is desirably generally parallel to the longitudinal axis 22 of the undergarment 20 and directed toward the opposite or front end edge 26 of the undergarment. Alternately, however, the loop tip orientation of either loop fastener 52 in the back waist region 32 could be generally parallel to the transverse axis 24 of the undergarment 20 and directed toward the other loop fastener 52 in the back waist region. Further arrangements of the loop fasteners are disclosed in U.S. Pat. No. 5,386,595 to Kuen et al., which is incorporated herein by reference.

Desirably although not necessarily, the loop fasteners 52 are bonded to the moisture barrier 40 with an adhesive substance. The adhesive substance may comprise any suitable adhesive such as a hot melt, or the like. By way of illustration, the adhesive substance may comprise a styrene-isoprene-styrene rubber block copolymer based adhesive containing a rosin ester tackifying resin. One suitable adhesive is available from Findley Adhesives, Inc. of Wauwatosa, Wis., USA, under the trade designation H2122. The adhesive substance may include zones having different basis weights of adhesive or other beneficial arrangements as disclosed in U.S. Pat. No. 5,476,702 to P. Datta et al., which is incorporated herein by reference.

Figure 1:
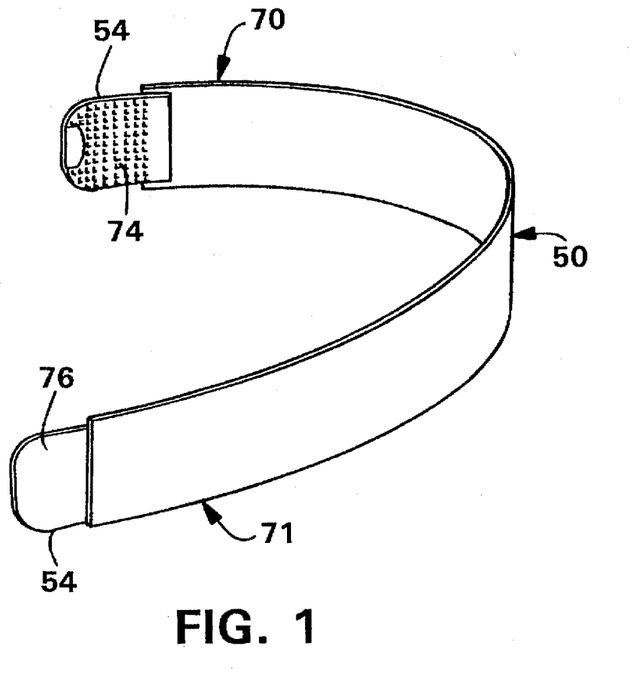
FIG. 1 representatively shows a perspective view of a strap member of a disposable absorbent article according to the present invention.

With particular reference to FIGS. 1, 2 and 6, the strap members 50 are each generally rectangular strips of material having opposite forward and rearward end portions 70 and 71. The strap members 50 are preferably formed of an elastic material, which is capable of stretching to approximately 2.8 to 3 times its relaxed length. The strap members 50 preferably have a longer length dimension of from about 6 inches to about 16 inches (15–41 cm.), and a smaller width dimension of from about 0.5 inch to about 2 inches (1–5 cm.). For example, each strap member 50 may be 10.5 inches (26.7 cm.) long and 1.5 inches (3.8 cm.) wide. The cut ends of the strap members 50 may be bonded by ultrasonic bonds, adhesives or other suitable means to prevent raveling.

The second interlocking fastening components or hook fasteners 54 are attached at each end portion 70 and 71 of each strap member 50, on the same side of the strap member. The hook fasteners 54 desirably comprise a single-sided hook material and form the hook component of the hook-and-loop attachment system. The term "hook material" is intended to mean any fabric or material having a base or backing structure and a plurality of hook members extending upwardly from at least one surface of the backing structure.

In contrast to the first interlocking fasteners 52 which desirably comprise a flexible fabric, the second interlocking fasteners 54 advantageously comprise a resilient material to minimize unintentional disengagement of the fastener components as a result of the second interlocking fastening component becoming deformed and catching on clothing or other items. The term "resilient" as used herein refers to an interlocking material having a predetermined shape and the property of the interlocking material to resume the predetermined shape after being engaged and disengaged from a mating, complementary interlocking material.

With a particular reference to FIGS. 1 and 2, each hook fastener 54 comprises a backing structure 72 having a first major surface 74 and an opposite second major surface 76. A plurality of engaging elements in the form of hooks 78 project upwardly from the first major surface 74. Each hook fastener 54 has a longitudinal axis or center line 80 parallel to the length dimension of the strap member 50 when laid flat and a transverse axis or center line 82 which intersects the longitudinal axis at a 90 degree angle (FIG. 2). In alternative embodiments, the backing structure 72 may have an inwardly curved configuration, in which case the longitudinal and transverse axis 80 and 82 are more appropriately considered primary and secondary meridians of the hook fastener. Such curved configurations for the hook fasteners 54 are disclosed in U.S. patent application Ser. No. 08/579,394 titled "Absorbent Article Fastening System And Its Method Of Manufacture" and filed Dec. 27, 1995, by P. Datta et al. (Attorney Docket No. 11,305) and assigned to the assignee of the present application.

Each hook fastener 54 includes a proximal edge 84, a distal edge 86 longitudinally spaced from the proximal edge, and first and second side edges 88 and 89 which extend between the proximal and distal edges. The proximal edge 84 is disposed nearest the central portion and opposite end portion of the strap member 50, while the distal edge 86 of the hook fastener is illustrated in the present embodiment as disposed beyond the end of the elastic strap material.

In one aspect of the present invention, the distal edge 86 and the first and second side edges 88 and 89 of each hook fastener 54 form rounded corners 90. In particular, the shape of the corner 90 is comparable to a circle segment having a radius of from about 0.6 to about 1.75 cm., and more particularly having a radius of from about 1.3 to about 1.75 cm.

As best illustrated in FIG. 2, each hook fastener 54 includes a grasping section 92 and an attachment section 94. The grasping section 92 is void of hooks 78 and provides a convenient surface for grasping the hook fastener 54 to remove it from engagement with a loop fastener 52. The grasping section 92 is contiguous with the distal edge 86 of the backing structure 72 and extends longitudinally inward to the attachment section 94. The grasping section 92 suitably has a surface area of at least about 0.4 cm$^2$, and particularly at least about 0.8 cm$^2$, such as from about 0.8 to about 1.6 cm$^2$ for improved performance. The shape of the grasping section 92 is illustrated as truncated semi-circular, and desirably has a maximum width dimension measured parallel to the transverse axis 82 of at least about 1.5 centimeters and a maximum length dimension measured parallel to the longitudinal axis 80 of at least about 0.6 centimeters. Suitable maximum length dimensions are at least about 0.3 centimeters, but are desirably from about 0.6 to about 1.0 centimeters. The maximum width dimension is desirably from about 1.6 to about 2.0 centimeters. The grasping section 92 is located along the longitudinal axis 80 of the hook fastener 54 so that upward force applied to the grasping section initiates a peel mode disengagement from the loop fastener 52.

The attachment section 94 of each hook fastener 54 comprises a primary attachment section 96 and a pair of secondary attachment sections 97 and 98. The primary attachment section 96 is longitudinally disposed between the grasping section 92 and the proximal edge 94 of the hook fastener 54. The secondary attachment sections 97 and 98 of each hook fastener 54 comprise those portions of the hook fastener that are transversely disposed between the grasping section 92 and each of the first and second side edges 88 and 89. Thus, for purposes of the present invention, the secondary attachment sections 97 and 98 comprise only those portions of the hook fastener that am transversely outward from the grasping section 92 and do not include any portions of the hook fastener that are disposed beyond the longitudinal extent of the grasping section. The grasping section 92 is spaced transversely inward from each of the first and second side edges 88 and 89 and positioned between the secondary attachment sections 97 and 98.

Each of the primary and secondary attachment sections 96, 97 and 98 comprise a plurality of hooks 78. Accordingly, since the grasping section 92 is void of hooks 78, the hooks am disposed exclusively in the primary attachment section 96 and the secondary attachment sections 97 and 98.

The hook fasteners 54 may be formed in a variety of shapes and sizes, such as generally rectangular and having a maximum length dimension of about 3.3 cm. and a maximum width dimension of about 3.5 cm. To facilitate secure engagement of the hook fasteners 54 to the loop fasteners 52, the primary attachment section 98 suitably has a surface area of at least about 60 percent, and particularly from about 60 to about 90 percent, of the total useable surface area, for example about 80 percent. Further, to minimize the incidence of fastener pop-offs, each of the secondary attachment sections suitably has a surface area of at least about 2 percent, such as from about 5 to about 10 percent, of the total useable surface area, and the corners 90 are formed with the exaggerated radius as noted above.

The hook fasteners 54 may be positioned in full face-to-face contact with the strap members 50 (not shown), or positioned such that hook fasteners extend past the ends of the strap members (FIGS. 1 and 2). The hook fasteners 54 may be attached to the strap members 50 by ultrasonic bonds, adhesives, stitches or other suitable means, and may include an attachment region 99 that is void of hooks (FIG. 2). For example, the hook fasteners 54 may be ultrasonically bonded to the strap members 50 during which process hooks present adjacent the proximal edge 54 are melted into the backing structure 72 to form the attachment region 99. The term "useable surface area" is employed herein to refer to the surface area of a hook fastener excluding the attachment region 99.

Suitable hook material may be molded or extruded of nylon, polypropylene or another suitable material. Desirable stiffness levels of the hook material may be obtained from polymeric materials having a flexural modulus of about 70,000–120,000 pounds per square inch ($4.83 \times 10^8$–$8.27 \times 10^8$ nt/m$^2$) and a Shore hardness value within the range of about D-40 to D-80, such as D-61. As illustrated in FIG. 2, the hook fasteners 54 may contain uni-directional hooks, with the machine direction of the hooks aligned with the longitudinal axis 80, and the hooks directed toward the opposite end portion 71 of the strap member 50. One suitable single-sided hook material for the hook fasteners 54 is available from Velcro Industries B.V., Amsterdam, Netherlands or affiliates thereof, and is identified as HTH-840 with 22 Series hooks in a uni-directional hook pattern.

The shape, density and polymer composition of the hooks may be selected to obtain the desired peel and shear force resistance values between the hook fasteners 54 and the loop fasteners 52. One skilled in the art would recognize, for instance, that a more aggressive hook material may comprises a material with a greater average hook height, a greater percentage of directionally-aligned hooks, or a more aggressive hook shape. As one example, the density of the hook members may be more than 50 hooks per square inch (8 per square cm.), and more particularly within the range of about 440 to about 1040 hooks per square inch (68–161 per square cm.), such as about 740 hooks per square inch (115 per square cm.). The row density may be within the range of about 20 to about 60 rows per linear inch of width (8–24 per linear cm.), such as about 40 rows per linear inch of width (16 per linear cm.). The hook members may be hook-shaped, mushroom-shaped, arrow-shaped or any other desired shape.

In use, the undergarment 20 is positioned on the body of the wearer and secured in position using the attachment system. The wearer can engage one hook fastener 54 of each strap member 50 with one of the loop fasteners 52 in the back waist region 32. After stretching or relaxing the strap members 50 to obtain the desired tension therein, the wearer can then engage the opposite hook fasteners 54 of each strap member 50 with one of the corresponding loop fasteners 52 in the front waist region 30. The angled orientation of the loop fasteners 52 prompts the wearer to secure the hook fasteners 54 so that the strap members 50 are aligned with the longitudinal axis of the front loop fasteners 52, beneficially causing the strap members to be positioned toward the hips of the wearer.

The configuration of the hook fasteners 54 enables them to resist accidental disengagement from the corresponding loop fasteners 52 as a result of snagging on clothing, bedding, or the like during use. The combination of the corners 90 having the relatively large radius of curvature and the incorporation of hooks 78 in the secondary attachment sections 97 and 98 reduce the likelihood that the corners will snag and accidentally dislodge the hook from the loop. Furthermore, the location of the grasping section 92 is readily accessible to the wearer. Insertion of the wearer's finger or fingernail beneath the grasping section 92 readily initiates a peeling motion to disengage the hook fastener 54 from the loop fastener 52.

Figure 3:
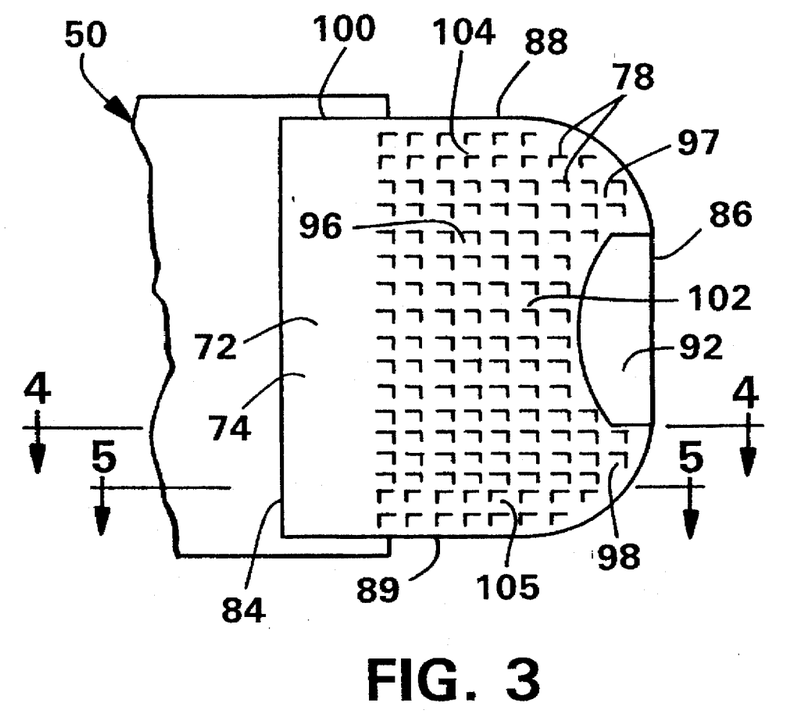
FIG. 3 representatively shows an enlarged plan view similar to FIG. 2 but illustrating one end portion of an alternative strap member.
Figure 4:
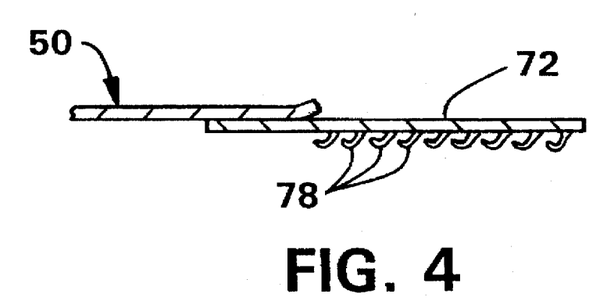
FIG. 4 representatively shows a section view taken generally from the plane of the line 4—4 in FIG. 3.
Figure 5:
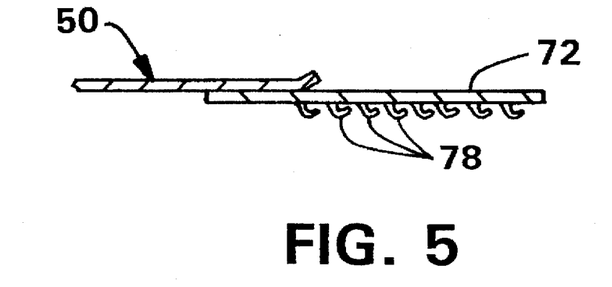
FIG. 5 representatively shows a section view taken generally from the plane of the line 5—5 in FIG. 3.

An alternative second interlocking fastening component in the form of a hook fastener 100 is illustrated in FIGS. 3–5. Components similar to those previously described have been given the same reference numeral. The fastener 100 includes a backing structure 72 with a plurality of hooks 78 projecting from the backing structure on a first major surface 74. The hooks 78 are disposed exclusively in a primary attachment section 96 and secondary attachment sections 97 and 98, but are not present in a grasping section 92.

In contrast to the embodiment of FIG. 2, however, the hooks 78 comprise both hooks which are directed toward the proximal edge 84 of the hook fastener 54 and hooks which are directed toward the distal edge 86 of the hook fastener. The attachment section 94 of the hook fastener 100 can be considered to include a medial region 102 and a pair of lateral regions 104 and 105. The lateral regions 104 and 105 are contiguous with the respective side edges 88 and 89 of the hook fastener 100 and include at least about 5 to 10 rows of hooks transversely inward from each side edge. Substantially all of the hooks 78 in each of the lateral regions 104 and 105, for example 100 percent of the hooks as illustrated in FIGS. 3 and 5, are directed toward the distal edge 86 of the hook fastener 100. FIG. 5 illustrates a section view through a lateral region 105 of the hook fastener 100 and more clearly illustrates the direction of the hooks 78. The direction of a hook 78 refers to the location of the head of the hook relative to the base of the hook.

The medial region 102 of hook fastener 100 consists of all remaining portions of the attachment section 94 that are disposed between the lateral regions 104 and 105. Substantially all of the hooks 78 in the medial region 102, and most desirably 100 percent of the hooks as illustrated in FIGS. 3 and 4, are directed toward the proximal edge of 84 of the hook fastener 100. By reversing the direction of hook 78 in the lateral regions 104 and 105 as compared to the medial region 102, the hook fastener 100 is further stabilized against clothing or other objects which may pass over the top of the fastener. The depiction of hooks 78 in the Figures is intended to facilitate understanding of the invention and is not intended to accurately reflect the number or size of the hooks.

Figure 9:
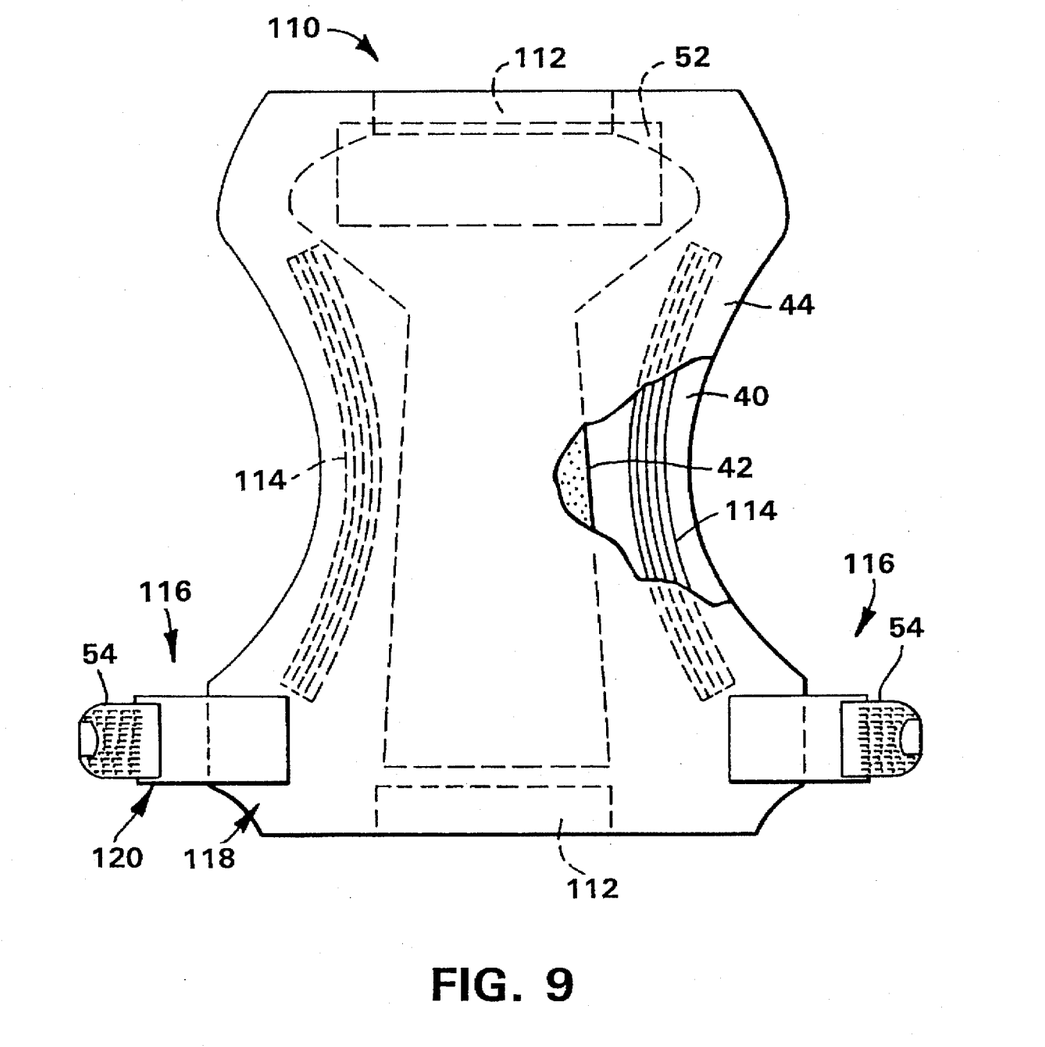
FIG. 9 representatively shows a plan view of an alternative disposable absorbent article according to the present invention, taken from the inner bodyside of the absorbent article in a stretched and laid flat condition and with portions broken away for purposes of illustration.

An alternative absorbent article according to the present invention is illustrated by a diaper 110 in FIG. 9. The diaper 110 includes a moisture barrier 40, a bodyside liner 44, and an absorbent assembly 42 disposed between the moisture barrier and bodyside liner. The diaper 110 may optionally contain waist elastics 112 and leg elastics 114. The diaper 110 also comprises fastening tabs 116 having a manufacturer's bond end 118 bonded to the diaper and a user's end 120 adapted to secure the diaper about the waist of the wearer. A first interlocking fastening component such as loop fastener 52 is bonded to the moisture barrier 40 in the waist region opposite the fastening tabs 116.

The user's end 120 refers to the portion of the fastening tab 116 that is used by the consumer to fasten the diaper about the waist of the wearer. The user's end 120 comprises an interlocking fastening component such as the hook fastener 54 illustrated in FIGS. 2 or 3 that is adapted to refastenably attach to the loop fastener 52. The hook fastener 54 is desirably formed with a grasping section 92, a primary attachment section 96, and secondary attachments 97 and 98 as described above in relation to FIG. 2. In addition, the hook fastener 54 may also include the reverse-oriented hooks 78 as described in relation to the medial region 102 and lateral regions 104 and 105 of FIGS. 3–5.

Figure 10:
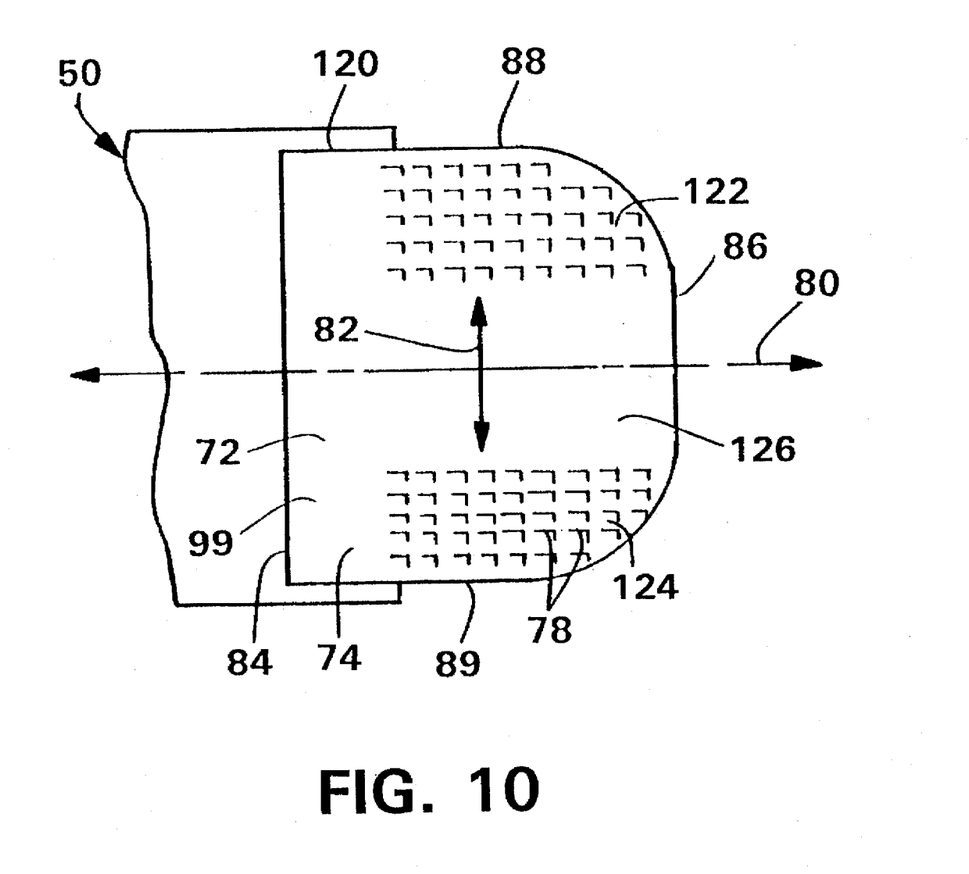
FIG. 10 representatively shows an enlarged plan view similar to FIG. 2 but illustrating one end portion of a further alternative strap member.

A further alternative hook fastener 120 is illustrated in FIG. 10. The fastener 120 includes a backing structure 72 with a plurality of hooks 78 projecting from the backing structure on a first major surface 74. The hooks 78 are disposed exclusively in first and second lateral attachment regions 122 and 124, but are not present in a grasping section 126.

The backing structure 72 of the hook fastener 120 includes the first and second lateral attachment regions 122 and 124, the grasping section 126, and an attachment region 99. The grasping section 126 is disposed between the proximal and distal edges 84 and 86 and is contiguous with the distal edge 86 and the attachment region 99 and/or the proximal edge 84. Thus, there are no hooks 78 present in the region along the longitudinal axis 80 of the hook fastener 120. The first lateral region 122 is contiguous with the first side edge 88 and extends transversely inward therefrom to the grasping section 126. The second lateral region 124 is contiguous with the second side edge 89 and extends transversely inward therefrom to the grasping section 126.

The grasping section 126 of the hook fastener 120 suitably has a surface area of from about 25 to about 60 percent of the total useable surface area of the fastener, and particularly from about 25 to about 50 percent of the total useable surface area. Each of the lateral regions 122 and 124 suitably have a surface area of from about 20 to about to about 40 percent of the total useable surface area of the fastener, and particularly from about 25 to about 35 percent of the total useable surface area.

In general, interlocking fastening components 54 having the above-described properties may be used with a variety of disposable absorbent products. Examples of diaper configurations, for instance, are disclosed in U.S. patent application Ser. No. 08/168,615 by T. Roessler et al., filed Dec. 16, 1993, and titled "Dynamic Fitting Diaper" (Attorney Docket No. 10,961); and U.S. patent application Ser. No. 08/288,167 by E. D. Johnson et al., filed Aug. 12, 1994, and titled "Diaper With Improved Lateral Elongation Characteristics" (Attorney Docket No. 11,629). The interlocking fastening components 54 may also be employed on absorbent articles that use a belt or single strap system (not shown). Examples of fitted brief configurations are disclosed in U.S. Pat. No. 4,500,316 to Damico.

Each of the foregoing or similar embodiments of the invention may be constructed by providing each of the individual components and bonding them together in the manner set forth above. The second interlocking fastening components 54 may be cut to the desired shape by any suitable cutting or stamping operation. The grasping sections 92 of the fastening components 54 may be formed by initially producing a region of the fastener that is void of hooks or alternatively removing hooks from a region to create the grasping section. For example, hooks may be removed from a region of the fastener to create the grasping section 92 by grinding, ultrasonically melting, or other suitable means.

Having thus described the present invention and the process for making it, a number of examples were prepared to give a more detailed understanding of the invention. These examples and the test procedures for measuring them are set forth below. The particular amounts, proportions, compositions and parameters are meant to be exemplary, and are not intended to specifically limit the scope of the invention.

EXAMPLES

A test was conducted to compare under simulated use conditions the operation of strap members having hook fasteners according to one embodiment of the present invention to strap members using conventional commercial hook fasteners. The strap members were tested in a laboratory with identical undergarments 20 having the general configuration as shown in FIG. 7. The strap members 50 with hook fasteners 54 of the type shown in FIG. 2 are referred to as Example A Straps, and the strap members with conventional hook fasteners are designated Control A Straps.

The undergarments 20 used in this test included a moisture barrier 40 which comprised an adhesive laminate of a polyethylene film inner layer and a spunbond nonwoven outer layer. An absorbent assembly 42 was disposed on the moisture barrier 40 and a spunbond polypropylene bodyside liner 44 was disposed on the absorbent assembly. The bodyside liner 44, absorbent assembly 42 and moisture barrier 40 were bonded together using a construction adhesive. The undergarments also included leg elastic members 46 secured along the two side margins 38 of the garment.

The fastening system for the undergarments included four first interlocking fastening components in the form of loop fasteners 52 bonded to the moisture barrier 40 with a hot melt adhesive. The loop fasteners 52 comprised a tricot warp knit, brushed (napped) polyester yarn fabric purchased from Guilford Mills (No. 33517). A vinyl acetate copolymer sizing (RESYN 5904 from National Starch and Chemical Corp.) had been mist deposited on the back face of the loop material prior to heat treatment to obtain a final concentration of less than about 4 weight percent. The two loop fasteners 52 in the front waist region 30 measured 1.25 by 3.37 inches (3.18 by 8.56 cm) and were positioned to form an angle of about 33 degrees with the transverse axis. The two loop fasteners 52 in the back waist region 32 measured 1.5 by 2.0 inches (3.8 by 5.1 cm) and were aligned with the transverse axis 24 of the garment.

The Control A Straps included two elastic strap members formed of an elastic material purchased from Shelby Elastics of Shelby, N.C., USA. The Control A Straps had a length of about 10.5 inches (26 cm.) and a width of about 1 inch (2.5 cm.). The strap ends were ultrasonically bonded to prevent raveling. The second interlocking fastening components were in the form of hook fasteners bonded at the ends of the strap members. The hook material was purchased from Velcro USA and identified as No. HTH-840 including 22 Series hooks. The hook fasteners measured 0.876 by 1.625 inches (2.23 by 4.13 cm) and had the unidirectional hooks pointing toward the center of the strap. Each hook fastener of the Control A Straps had three rows of hooks adjacent the distal edge ultrasonically deformed between the side edges to form a grasping section. The Control A Straps were representative of straps being supplied by Kimberly-Clark Corporation of Neenah, Wis., with adult incontinence products sold under the tradename DEPEND® EasyFit Undergarments in August of 1995.

The Example A Straps were identical to the Control A Straps with the exception of the hook fasteners 54. Each of the hook fasteners 54 of the Example A Straps included a grasping section that was void of hooks and contiguous with the distal edge of the fastener. Each hook fastener 54 also included primary and secondary attachment sections 96, 97 and 98 generally as described in relation to FIG. 2. Hooks were disposed exclusively in the primary and secondary attachment sections.

This test used 25 female participants. Each participant wore one undergarment with one pair of Example A Straps and one undergarment with one pair of Control A Straps. After donning each undergarment with a pair of strap members, each participant applied an appropriately sized pair of cotton underwear over the top of the undergarment. Participants were instructed to pull the underwear down past the knees and up to the waist a total of four times in succession, followed by removing and reattaching the hook fasteners to the front and back loop fasteners by grasping the grasping sections of the hook fasteners. Each cycle of pulling up and down the cotton underwear and detaching and reattaching the fasteners was repeated for a total of eight cycles in a one day period. This procedure was repeated the following day with a new undergarment and a new pair of strap members.

Throughout the procedure, participants were requested to observe and document the instances of pop-offs for both the Control A and the Example A Straps. The Example A Straps experienced 12 pop-offs and the Control A Straps experienced 48 pop-offs, representing a significant difference between mechanical fastener designs.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

I claim:

1. An absorbent article, comprising:

a garment comprising a moisture barrier, a bodyside liner, and an absorbent assembly between said moisture barrier and said bodyside liner, the garment having first and second waist regions and an intermediate section which interconnects the waist regions;

at least one first interlocking fastening component disposed in the first and second waist regions; and a pair of strap members, each strap member having opposite forward and rearward end portions and comprising a second interlocking fastening component bonded to each of the forward and rearward end portions, each second interlocking fastening component adapted to refastenably engage the first interlocking fastening component, each second interlocking fastening component having a longitudinal axis, a transverse axis, a proximal edge, a distal edge longitudinally spaced from the proximal edge, and first and second side edges extending between the proximal and distal edges, each second interlocking fastening component comprising:

a backing substrate having a grasping section contiguous with the distal edge, a primary attachment section longitudinally disposed between the grasping section and the proximal edge, and secondary attachment sections transversely disposed between the grasping section and each of the first and second side edges; and a plurality of upstanding engaging elements disposed exclusively in the primary attachment section and each of the secondary attachment sections.

2. The absorbent article of claim 1, wherein each secondary attachment section has a surface area of at least about 2 percent of a total useable surface area.

3. The absorbent article of claim 2, wherein each secondary attachment section has a surface area of from about 5 to about 10 percent of the total useable surface area.

4. The absorbent article of claim 1, wherein each grasping section has a surface area of at least about 10 percent of a total useable surface area.

5. The absorbent article of claim 4, wherein each grasping section has a surface area of from about 10 to about 25 percent of the total useable surface area.

6. The absorbent article of claim 4, wherein each grasping section has a maximum width dimension of at least about 1.5 centimeters and a maximum length dimension of at least about 0.6 centimeters.

7. The absorbent article of claim 1, wherein:

the backing substrate has an attachment section that consists of the primary attachment section and the secondary attachment sections, the attachment section defining a medial region, a first lateral region contiguous with the first side edge, and a second lateral region contiguous with the second side edge and disposed between the second side edge and the medial region;

a plurality of upstanding engaging elements directed toward the proximal edge are disposed in the medial region; and a plurality of upstanding engaging elements directed toward the distal edge are disposed in each of the first and second lateral regions.

8. An absorbent article, comprising:

a garment comprising a moisture barrier, a bodyside liner, and an absorbent assembly between said moisture barrier and said bodyside liner, the garment having first and second waist regions and an intermediate section which interconnects the waist regions;

at least one first interlocking fastening component disposed in the first and second waist regions; and a pair of strap members, each strap member having opposite forward and rearward end portions and comprising a second interlocking fastening component bonded to each of the forward and rearward end portions, each second interlocking fastening component adapted to refastenably engage the first interlocking fastening component, each second interlocking fastening component having a longitudinal axis, a transverse axis, a proximal edge, a distal edge longitudinally spaced from the proximal edge, and first and second side edges extending between the proximal and distal edges, each second interlocking fastening component comprising:

a backing substrate having a grasping section disposed between the proximal and distal edges, a first lateral region contiguous with the first side edge and transversely disposed between the first side edge and the grasping section, and a second lateral region contiguous with the second side edge and transversely disposed between the second side edge and the grasping section; and a plurality of upstanding engaging elements disposed exclusively in the first and second lateral regions.

9. The absorbent article of claim 8, wherein the grasping section has a surface area of from about 25 to about 60 percent of a total useable surface area.

10. The absorbent article of claim 8, wherein each of the first and second lateral regions has a surface area of from about 20 to about 40 percent of a total useable surface area.

11. The absorbent article of claim 8, wherein each of the first and second lateral regions has a surface area of from about 25 to about 35 percent of a total useable surface area.

12. The absorbent article of claim 1 or 8, wherein the distal edge and the first and second side edges of each second interlocking fastening component form rounded corners having a radius of from about 1.3 to about 1.75 centimeters.

13. The absorbent article of claim 1 or 8, wherein the first interlocking fastening component comprises a flexible fabric.

14. The absorbent article of claim 13, wherein the first interlocking fastening component comprises a loop material and the second interlocking fastening component comprises a hook material.

* * * * *